US010260102B2

(12) United States Patent
Ma et al.

(10) Patent No.: US 10,260,102 B2
(45) Date of Patent: Apr. 16, 2019

(54) METHODS AND COMPOSITIONS FOR DETECTING MUTATION IN THE HUMAN EZH2 GENE

(71) Applicant: Roche Molecular Systems, Inc., Pleasanton, CA (US)

(72) Inventors: Xiaoju Max Ma, San Carlos, CA (US); Chitra Manohar, San Ramon, CA (US); Alison Tsan, Danville, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 281 days.

(21) Appl. No.: 14/508,618

(22) Filed: Oct. 7, 2014

(65) Prior Publication Data

US 2015/0099747 A1 Apr. 9, 2015

Related U.S. Application Data

(60) Provisional application No. 61/888,660, filed on Oct. 9, 2013.

(51) Int. Cl.
*A61K 31/496* (2006.01)
*C12Q 1/6886* (2018.01)
*A61K 31/4439* (2006.01)
*A61K 31/5377* (2006.01)

(52) U.S. Cl.
CPC ........ *C12Q 1/6886* (2013.01); *A61K 31/4439* (2013.01); *A61K 31/496* (2013.01); *A61K 31/5377* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 2006/0019256 A1* | 1/2006 | Clarke | ................. | C12N 5/0695 435/6.14 |
| 2009/0263811 A1 | 10/2009 | Kiyohara | | |
| 2015/0099747 A1 | 4/2015 | Ma et al. | | |

FOREIGN PATENT DOCUMENTS

| | | |
|---|---|---|
| CN | 101993934 | 3/2011 |
| WO | 0142498 A1 | 9/2002 |
| WO | 2013049770 A2 | 4/2013 |
| WO | 2013049770 A3 | 4/2013 |
| WO | WO2013086639 A1 * | 6/2013 ............ C12N 15/54 |
| WO | PCT/EP2014/071372 | 1/2015 |

OTHER PUBLICATIONS

Muzny, et al. Rattus, novegicus, GenBank Accesion: AC131602.4, submitted Jun. 7, 2003, pp. 1-61, available at ncbi.nlm.nih.gov (Year : 2003).*
Bodor, Csaba, et al., 2013, "EZH2 mutations are frequent and represent an early event in follicular lymphoma", Blood, 122(18):3165-3168.
Saieg, Mauro Ajaj, et al., 2013, "EZH2 and CD79B Mutational Status Over Time in B-Cell Non-Hodgkin Lymphomas Detected by High-Throughput Sequencing Using Minimal Samples", Cancer Cytopathology, 377-386.
Liu et al. (2012) Plant Methods 8:34.
Cha, R. S., et al., Mismatch Amplification Mutation Assay (MAMA): Application to the c-H-ras Gene, Genome Research, 1992, pp. 14-20, vol. 2.
Office action dated Sep. 3, 2018 received in corresponding Japanese patent application No. 2016-516945.
Chinese Office Action dated Jun. 29, 2018 in corresponding Chinese Patent Application No. 201480055312.0 filed on Oct. 7, 2014, pp. 1-15.
International Preliminary Report on Patentability dated Apr. 12, 2016 in corresponding PCT/EP2014/071372 filed on Oct. 7, 2014, pp. 1-7.
Lv, J., et al., Research progress in the relationship between EZH2 gene and tumor, Journal of Clinical Neurology, Apr. 30, 2012, pp. 154-156, vol. 25, No. 2.
Office Action Art. 94(3) EPC dated Apr. 21, 2017 in European Application No. 14781520.3, 8 pages.
Written Opinion dated Jan. 7, 2015 in corresponding PCT/EP2014/071372 filed on Oct. 7, 2014, pp. 1-6.
Japanese Office Action dated Sep. 11, 2018 in Application No. 2016-516945, 7 pages.
Koizumi, M., et al., Improvement of single nucleotide polymorphism genotyping by allele-speciWc PCR using primers modiWed with an ENA residue, Analytical Biochemistry, Mar. 14, 2005, pp. 287-294, vol. 340.

* cited by examiner

*Primary Examiner* — Sarae L Bausch
(74) *Attorney, Agent, or Firm* — Carol Johns; Olga Kay

(57) ABSTRACT

The invention comprises reagents and methods for detecting cancer-associated mutations in the human EZH2 gene. Further, a method of detecting the mutations and a method of treatment are disclosed.

12 Claims, No Drawings

Specification includes a Sequence Listing.

SEQUENCE LISTING

<160> NUMBER OF SEQ ID NOS: 85

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcagtgcctt acctctccac agtt                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcagtgcctt acctctccac agat                                            24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcagtgcctt acctctccac aggt                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcagtgcctt acctctccac agct                                            24

<210> SEQ ID NO 5
<211> LENGTH: 24
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 5
tcagtgcctt acctctccac aatt                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcagtgcctt acctctccac attt                                          24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcagtgcctt acctctccac actt                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcagtgcctt acctctccac ggtt                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcagtgcctt acctctccac tgtt                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcagtgcctt acctctccac cgtt                                          24

<210> SEQ ID NO 11
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 11
agtgccttac ctctccacag tg                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtgccttac ctctccacag ag                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agtgccttac ctctccacag gg                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agtgccttac ctctccacag cg                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agtgccttac ctctccacaa tg                                              22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agtgccttac ctctccacat tg                                              22

<210> SEQ ID NO 17
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 17
agtgccttac ctctccacac tg                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agtgccttac ctctccacgg tg                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agtgccttac ctctccactg tg                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agtgccttac ctctccaccg tg                                              22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcagtgcctt acctctccac aga                                             23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcagtgcctt acctctccac aaa                                             23

<210> SEQ ID NO 23
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 23
tcagtgcctt acctctccac ata                                              23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcagtgcctt acctctccac aca                                              23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcagtgcctt acctctccac gga                                              23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcagtgcctt acctctccac tga                                              23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcagtgcctt acctctccac cga                                              23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcagtgcctt acctctccaa aga                                              23

<210> SEQ ID NO 29
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 29
tcagtgcctt acctctccag aga                                              23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcagtgcctt acctctccat aga                                              23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcagtgcctt acctctccac agg                                              23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tcagtgcctt acctctccac aag                                              23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcagtgcctt acctctccac atg                                              23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcagtgcctt acctctccac acg                                              23

<210> SEQ ID NO 35
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 35
tcagtgcctt acctctccac tgg                                              23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcagtgcctt acctctccac cgg                                              23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcagtgcctt acctctccac ggg                                              23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcagtgcctt acctctccaa agg                                              23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcagtgcctt acctctccat agg                                              23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcagtgcctt acctctccag agg                                              23

<210> SEQ ID NO 41
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 41
agtgccttac ctctccacag c                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agtgccttac ctctccacaa c                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agtgccttac ctctccacat c                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agtgccttac ctctccacac c                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agtgccttac ctctccactg c                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agtgccttac ctctccaccg c                                              21

<210> SEQ ID NO 47
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 47
agtgccttac ctctccacgg c                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agtgccttac ctctccagag c                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agtgccttac ctctccaaag c                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agtgccttac ctctccatag c                                              21

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcagtgcctt acctctccac agta                                           24

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
attgctggca ccatctgacg t                                              21

<210> SEQ ID NO 53
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 53
tttatcaaag atcctgtgca gaaaaatgaa ttcatctca                          39

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
tttatcaaag atcctgtgca gaaaaatgaa ttcatctca                          39

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ttgctggcac catctgacgt g                                             21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tattgctggc accatctgac g                                             21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctattgctgg caccatctga c                                             21

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cgaattttgt tacccttgcg ggttg                                         25

<210> SEQ ID NO 59
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 59
cgaattttgt taccctthgcg ggttc                                          25

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cgaattttgt taccctthgcg ggtac                                          25

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cgaattttgt taccctthgcg ggtcc                                          25

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgaattttgt taccctthgcg ggtgc                                          25

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cgaattttgt taccctthgcg ggatc                                          25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgaattttgt taccctthgcg ggctc                                          25

<210> SEQ ID NO 65
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 65
cgaattttgt taccttgcg gggtc                                              25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cgaattttgt taccttgcg gattc                                              25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cgaattttgt taccttgcg gtttc                                              25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cgaattttgt taccttgcg gcttc                                              25

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtttacttat aactgaaatt attcactggg c                                      31

<210> SEQ ID NO 70
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
tgcttacttt tttctttta gattttgtgg tgga                                    34

<210> SEQ ID NO 71
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 71
tgcttacttt tttctttta gattttgtgg tgga                                    34

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tagcagtttg gatttaccga atgatttg                                          28

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tagcagtttg gatttaccga atgattta                                          28

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tagcagtttg gatttaccga atgattaa                                          28

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tagcagtttg gatttaccga atgattca                                          28

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tagcagtttg gatttaccga atgattga                                          28

<210> SEQ ID NO 77
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 77
tagcagtttg gatttaccga atgatata                                              28

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tagcagtttg gatttaccga atgatcta                                              28

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tagcagtttg gatttaccga atgatgta                                              28

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tagcagtttg gatttaccga atgaatta                                              28

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tagcagtttg gatttaccga atgactta                                              28

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tagcagtttg gatttaccga atgagtta                                              28

<210> SEQ ID NO 83
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 83
tagcagtttg gatttaccga atgatta                                            27

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cactgggctg tgcttacttt tttc                                               24

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
tttagatttt gtggtggatg caacccgcaa                                         30
```

METHODS AND COMPOSITIONS FOR DETECTING MUTATION IN THE HUMAN EZH2 GENE

SEQUENCE LISTING

The instant application contains a Sequence Listing which has been submitted electronically in ASCII format and is hereby incorporated by reference in its entirety. Said ASCII copy, created on Aug. 22, 2014, is named 31749-US1_SL.txt and is 19,506 bytes in size.

FIELD OF THE INVENTION

The invention relates to cancer diagnostics and companion diagnostics for cancer therapies. In particular, the invention relates to the detection of mutations that are useful for diagnosis and prognosis as well as predicting the effectiveness of treatment of cancer.

BACKGROUND OF THE INVENTION

EZH2 is a chromatin-modifying enzyme targeting histone proteins. Specifically, EZH2 protein is the catalytic subunit of Polycomb Repressive Complex 2 (PRC2), which is a histone methyltransferase specific for lysine-27 (K27) of histone 3 (H3). Methylated H3-K27 is associated with gene repression. Abnormally elevated levels of EZH2 have been found in various cancer tissues and are associated with gene repression, reviewed in Simon, J., and Lange, C. (2008) *Roles of EZH2 histone methyltransferase in cancer epigenetics*, Mut. Res. 647:21. It was also discovered that specific mutations alter the histone-modifying function of EZH2 protein by altering its substrate preference. EZH2 mutated at position Y646 (see Wiggle, T., et al. (2011) FEBS Lett. 585:3011) is abnormally active at methylating di-methylated H3 (H3K27me2) into the tri-methylated form (H3K27me3). EZH2 mutated at position A692 (see Majer, C., et al. (2012) FEBS Lett, 586:3348) is abnormally active at di-methylation; and EZH2 mutated at position A682 (see McCabe, M., et al. (2012), PNAS 109:2989) is abnormally active at all three methylation steps. In human cancer, these mutations have been shown to promote gene repression via histone hypermethylation.

Therapies targeting EZH2 have been developed. Selective small molecules inhibitors of EZH2 have been shown to block EZH2 (and PRC2) activity and promote killing of cancer cells in vitro. (Knutson, S, et al. (2012) Nature Chem. Bio. 8:890. The inhibitor is uniquely effective at killing cells with abnormally active mutant EZH2 without affecting cells with wild-type EZH2 (Id.) Therefore, a companion diagnostic test is necessary to identify patients whose tumors have mutant EZH2 and will likely benefit from the EZH2 inhibitors. It is essential that a clinical test for EZH2 mutations target as many mutations as possible with adequate sensitivity. This will assure that patients with rare mutations do not receive a "false negative" test result and miss out on a potentially life-saving treatment. At the same time, the test should be highly specific to ensure that patients do not receive a "false positive" result and receive costly and ineffective treatment.

One technique that is sensitive and amenable to multiplexing is allele-specific PCR (AS-PCR). This technique detects mutations or polymorphisms in nucleic acid sequences in the presence of wild-type variants of the sequences. In a successful allele-specific PCR, the desired variant of the target nucleic acid is amplified, while the other variants are not, at least not to a detectable level. In an allele-specific PCR, at least one primer is allele-specific such that primer extension occurs only when the specific variant of the sequence is present. One or more allele-specific primers targeting one or more polymorphic sites can be present in the same reaction mixture. Design of successful allele-specific primers is an unpredictable art. While it is routine to design a primer for a known sequence, no formula exists for designing a primer that can discriminate between very similar sequences.

In the context of a diagnostic assay, precise discrimination is required. For example, in the context of the EZH2 mutation detection, the performance of the allele-specific primer may determine the course of a patient's cancer therapy. Thus there is a need for a comprehensive assay capable of detecting a maximum number of EZH2 mutations with maximum specificity and sensitivity.

SUMMARY OF THE INVENTION

In one embodiment, the invention is an isolated oligonucleotide for detecting mutations in the human EZH2 gene consisting of the sequence of an oligonucleotide selected from SEQ ID NOs corresponding to EZH2_Y646N_R (SEQ ID NO: 1), Y646H_R (SEQ ID NO: 12), Y646F_R (SEQ ID NO: 21), Y646C_R (SEQ ID NO: 41), A682G_R (SEQ ID NO: 59) and A692V_R (SEQ ID NO: 73) except comprising at least one mismatch with the naturally occurring sequences of the human EZH2 gene. In variations of this embodiment, the mismatch is located within the last 5 nucleotides at the 3'-end of the oligonucleotide. In further variations of this embodiment, the oligonucleotide further comprises at least one non-natural oligonucleotide.

In another embodiment, the invention is a method of detecting mutations in the human EZH2 nucleic acid in a sample comprising: (a) contacting the nucleic acid in the sample with at least one oligonucleotide of claim 1; (b) incubating the sample under conditions allowing hybridization of the oligonucleotide to the target sequence within the EZH2 nucleic acid; (c) generating of the amplification product containing the target sequence within the EZH2 nucleic acid; and (d) detecting the presence of the amplified product thereby detecting the presence of the mutation in the EZH2 nucleic acid. In variations of this embodiment, the nucleic acid in the sample is contacted with the oligonucleotide selected from allele-specific primers listed in Tables 2-4 and comprising at least one mismatch with the naturally occurring sequence of the human EZH2 gene.

In another embodiment, the invention is a method of determining whether a patient having a malignant tumor is likely to respond to EZH2 inhibitors, comprising: (a) contacting the nucleic acid in the sample from the patient with at least one oligonucleotide selected from allele-specific primers listed in Tables 2-4 and comprising at least one mismatch with the naturally occurring sequence of the human EZH2 gene; (b) incubating the sample under conditions allowing hybridization of the oligonucleotide to the target sequence within the EZH2 nucleic acid; and generation of the amplification product containing the target sequence within the EZH2 nucleic acid; (c) detecting the presence of the amplified product thereby detecting the presence of the mutation in the EZH2 nucleic acid, wherein the presence of the mutation indicates that the patient is likely to respond to EZH2 inhibitors. In variations of this embodiment, the oligonucleotides are specific for at least two of the mutations selected from mutations at positions Y646, A682 and A692. In further variations of this embodiment, the oligonucleotides are specific for at least two of the mutations selected from Y646N, Y646H, Y646S, Y646F, Y646C, A682G, and A692V.

In yet another embodiment, the invention is a kit for detecting mutations in the human EZH2 gene comprising at least one oligonucleotide selected from allele-specific primers listed in Tables 2-4 and comprising at least one mismatch with the naturally occurring sequence of the human EZH2 gene and optionally, at least one additional reagent for use in PCR. In variations of this embodiment, the kit comprises two or more of SEQ ID NOS 1-51, 58-68 and 72-83. In further variations of this embodiment, the kit comprises two or more oligonucleotides, each specific the mutation selected from mutations at positions Y646, A682 and A692. In further variations of this embodiment, the kit comprises two or more oligonucleotides, each specific the mutations selected from Y646N, Y646H, Y646S, Y646F, Y646C, A682G, and A692V.

In yet another embodiment, the invention is a method of treating as patient having a cancer comprising administering to the patient a suitable dose of an EZH2 inhibitor wherein the patient's tumor harbors a somatic mutation in the EZH2 gene detected with an oligonucleotide selected from allele-specific primers listed in Tables 2-4 and comprising at least one mismatch with the naturally occurring sequence of the human EZH2 gene.

In yet another embodiment, the invention is a method of treating a patient having a cancer comprising probing the patient's sample for mutations in the EZH2 gene using at least one oligonucleotide selected from allele-specific primers listed in Tables 2-4 and comprising at least one mismatch with the naturally occurring sequence of the human EZH2 gene, and if a mutation is found, administering to the patient a dose of EZH2 inhibitor. In variations of this embodiment, the mutation is at positions Y646, A682 and A692. In further variations of this embodiment, the mutation is selected from Y646N, Y646H, Y646S, Y646F, Y646C, A682G, and A692V. In further variations of this embodiment the oligonucleotide is selected from SEQ ID NOS 1-51, 58-68 and 72-83. In further variations of this embodiment, the inhibitor is selected from EI1 EPZ6438 (E7438), GSK343 or GSK126. In further variations of this embodiment, the cancer is lymphoma.

BRIEF DESCRIPTION OF THE DRAWINGS

None

DETAILED DESCRIPTION OF THE INVENTION

Definitions

To facilitate the understanding of this disclosure, the following definitions of the terms used herein are provided.

The term "X[n]Y" refers to a missense mutation that results in a substitution of amino acid X for amino acid Y at position [n] within the amino acid sequence. For example, the term "Y646C" refers to a mutation where tyrosine at position 646 is replaced with cysteine.

The term "allele-specific primer" or "AS primer" refers to a primer that hybridizes to more than one variant of the target sequence, but is capable of discriminating between the variants of the target sequence in that only with one of the variants, the primer is efficiently extended by the nucleic acid polymerase under suitable conditions. With other variants of the target sequence, the extension is less efficient or inefficient.

The term "common primer" refers to the second primer in the pair of primers that includes an allele-specific primer. The common primer is not allele-specific, i.e. does not discriminate between the variants of the target sequence between which the allele-specific primer discriminates.

The terms "complementary" or "complementarity" are used in reference to antiparallel strands of polynucleotides related by the Watson-Crick base-pairing rules. The terms "perfectly complementary" or "100% complementary" refer to complementary sequences that have Watson-Crick pairing of all the bases between the antiparallel strands, i.e. there are no mismatches between any two bases in the polynucleotide duplex. However, duplexes are formed between antiparallel strands even in the absence of perfect complementarity. The terms "partially complementary" or "incompletely complementary" refer to any alignment of bases between antiparallel polynucleotide strands that is less than 100% perfect (e.g., there exists at least one mismatch or unmatched base in the polynucleotide duplex). The duplexes between partially complementary strands are generally less stable than the duplexes between perfectly complementary strands.

The term "sample" refers to any composition containing or presumed to contain nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) or core needle biopsies and nucleic acids isolated therefrom.

The terms "polynucleotide" and "oligonucleotide" are used interchangeably. "Oligonucleotide" is a term sometimes used to describe a shorter polynucleotide. An oligonucleotide may be comprised of at least 6 nucleotides, for example at least about 10-12 nucleotides, or at least about 15-30 nucleotides corresponding to a region of the designated nucleotide sequence.

The term "primary sequence" refers to the sequence of nucleotides in a polynucleotide or oligonucleotide. Nucleotide modifications such as nitrogenous base modifications, sugar modifications or other backbone modifications are not a part of the primary sequence. Labels, such as chromophores conjugated to the oligonucleotides are also not a part of the primary sequence. Thus two oligonucleotides can share the same primary sequence but differ with respect to modifications and labels.

The term "primer" refers to an oligonucleotide which hybridizes with a sequence in the target nucleic acid and is capable of acting as a point of initiation of synthesis along a complementary strand of nucleic acid under conditions suitable for such synthesis. As used herein, the term "probe" refers to an oligonucleotide which hybridizes with a sequence in the target nucleic acid and is usually detectably labeled. The probe can have modifications, such as a 3'-terminus modification that makes the probe non-extendable by nucleic acid polymerases, and one or more chromophores. An oligonucleotide with the same sequence may serve as a primer in one assay and a probe in a different assay.

The term "mismatch" refers to lack of Watson-Crick base pairing between the complementary strands in the nucleic acid duplex. For example, a mismatch occurs where adenine (instead of guanine) occurs opposite cytosine in the complementary strand. If a single-stranded nucleic acid (such as an amplification primer) is said to have a mismatch, that means that when hybridized to its target sequence, the primer has a nucleotide with a base lacking Watson-Crick pairing with the corresponding base on the complementary strand.

As used herein, the term "target sequence", "target nucleic acid" or "target" refers to a portion of the nucleic acid sequence which is to be either amplified, detected or both.

The terms "hybridized" and "hybridization" refer to the base-pairing interaction of between two nucleic acids which results in formation of a duplex. It is not a requirement that two nucleic acids have 100% complementarity over their full length to achieve hybridization and strand extension.

Human EZH2 gene has been found frequently mutated in cancer. Table 1 shows the most common mutations described to date.

TABLE 1

Mutations in the human EZH2 gene

| Amino Acid | Codon |
|---|---|
| Y646 | TAC |
| Y646F | TTC |
| Y646N | AAC |
| Y646S | TCC |
| Y646H | CAC |
| Y646C | TGC |
| A692 | GCA |
| A692V | GTA |
| A682 | GCA |
| A682G | GGA |

Allele-specific PCR has been described in U.S. Pat. No. 6,627,402. In an allele-specific PCR, the discriminating primer has a sequence complementary to the desired variant of the target sequence, but mismatched with the undesired variants of the target sequence. Typically, the discriminating nucleotide in the primer, i.e. the nucleotide matching only one variant of the target sequence, is the 3'-terminal nucleotide. However, the 3' terminus of the primer is only one of many determinants of specificity. The specificity in an allele-specific PCR derives from the much slower rate of extension of the mismatched primer than of the matched primer, ultimately reducing the relative amplification efficiency of the mismatched target. The reduced extension kinetics and thus PCR specificity is influenced by many factors including the nature of the enzyme, reaction components and their concentrations, the extension temperature and the overall sequence context of the mismatch. The effect of these factors on each particular primer cannot be reliably quantified. Without a reliable quantitative strategy and with an enormous number of variables, the design of allele-specific primers is a matter of trial and error with often surprising results. In the case of mutant alleles of EZH2 described below, only a fraction of primers tested gave suitable performance, i.e. acceptable PCR efficiency and at the same time, discrimination between the mutant and the wild-type template.

One approach to increasing specificity of allele-specific primers is by including an internal mismatched nucleotide in addition to the terminal mismatch. See U.S. patent application Ser. No. 12/582,068 filed on Oct. 20, 2009, which is incorporated herein by reference in its entirety. The internal mismatched nucleotide in the primer may be mismatched with both the desired and the undesired target sequences. Because the mismatches destabilize the primer-template hybrids with both desired and undesired templates, some of the mismatches can prevent amplification of both templates and cause failure of the PCR. Therefore the effect of these internal mismatches on a particular allele-specific PCR primer cannot be predicted.

For successful extension of a primer, the primer needs to have at least partial complementarity to the target sequence. Generally, complementarity at the 3'-end of the primer is more critical than complementarity at the 5'-end of the primer. (Innis et al. Eds. *PCR Protocols*, (1990) Academic Press, Chapter 1, pp. 9-11). Therefore the present invention encompasses the primers disclosed in Tables 1-7 as well as the variants of these primers with 5'-end variations.

It has been previously described that for PCR amplification in general, primer specificity can be increased by the use of chemical modification of the nucleotides in the primer. The nucleotides with covalent modifications of the exocyclic amino groups and the use of such nucleotides in PCR have been described in U.S. Pat. No. 6,001,611, which is incorporated herein by reference in its entirety. Because the modifications disrupt Watson-Crick hydrogen bonding in primer-template hybrids with both desired and undesired templates, some of the modifications can prevent amplification of both templates and cause failure of the PCR. Therefore the effect of these covalent modifications on allele-specific PCR cannot be predicted.

In one embodiment the present invention comprises isolated oligonucleotides for simultaneously detecting multiple EZH2 mutations in a single tube. In one embodiment, the invention comprises isolated oligonucleotides for specifically detecting mutations at position Y646 in the human EZH2 gene (Table 2). In another embodiment, the invention comprises isolated oligonucleotides for specifically detecting mutations at position A682 in the human EZH2 gene (Table 3). In yet another embodiment, the invention comprises isolated oligonucleotides for specifically detecting mutations at position A692 in the human EZH2 gene (Table 4). Some of these oligonucleotide primers contain internal mismatches, e.g., nucleotides not present in naturally occurring mutant or wild-type sequences as shown in Tables 2-4. Some oligonucleotide primers contain non-natural nucleotides as shown in the tables.

As demonstrated by experimental results (Tables 5-7) performance of allele-specific primers designed according to the same principles varies greatly. The present invention involves isolated oligonucleotides, each specific for one of several closely related sequences (i.e., series of mutations at the single codon 646). As shown in Tables 5-7, the primers are uniquely able to distinguish their target mutation from similar mutations and from the wild-type sequence at the same codon.

As an option, in a polymerase chain reaction (PCR) assay, the allele-specific primers disclosed in Tables 2-4 may be paired with a "common" i.e., not allele-specific second primer disclosed in Tables 2-4 and where appropriate, with a detection probe also disclosed in Tables 2-4. One skilled in the art will immediately recognize that alternative common primers and detection probes may be designed and combined with the allele-specific primers of the present invention in order to detect mutations at positions Y646, A682 and A692 in the human EZH2 gene by AS-PCR.

TABLE 2

Oligonucleotides for detecting mutations at position Y646

| SEQ ID NO: | Oligo_ID | Sequence | MM* location and sequence |
|---|---|---|---|
| Allele-specific primers | | | |
| 1 | EZH2_Y646N_R: | TCAGTGCCTTACCTCTCCACAGTT | none |
| 2 | EZH2_Y646N_R1: | TCAGTGCCTTACCTCTCCACAGAT | n-1, AT |

TABLE 2-continued

Oligonucleotides for detecting mutations at position Y646

| | | | |
|---|---|---|---|
| 3 | EZH2_Y646N_R2 | TCAGTGCCTTACCTCTCCACAGGT | n-1, GT |
| 4 | EZH2_Y646N_R3 | TCAGTGCCTTACCTCTCCACAGCT | n-1, CT |
| 5 | EZH2_Y646N_R4 | TCAGTGCCTTACCTCTCCACAATT | n-2, AG |
| 6 | EZH2_Y646N_R5 | TCAGTGCCTTACCTCTCCACATTT | n-2, TG |
| 7 | EZH2_Y646N_R6 | TCAGTGCCTTACCTCTCCACACTT | n-2, CG |
| 8 | EZH2_Y646N_R7 | TCAGTGCCTTACCTCTCCACGGTT | n-3, GA |
| 9 | EZH2_Y646N_R8 | TCAGTGCCTTACCTCTCCACTGTT | n-3, TA |
| 10 | EZH2_Y646N_R9 | TCAGTGCCTTACCTCTCCACCGTT | n-3, CA |
| 11 | EZH2_Y646H_R | AGTGCCTTACCTCTCCACAGTG | none |
| 12 | EZH2_Y646H_R1 | AGTGCCTTACCTCTCCACAGAG | n-1, AT |
| 13 | EZH2_Y646H_R2 | AGTGCCTTACCTCTCCACAGGG | n-1, GT |
| 14 | EZH2_Y646H_R3 | AGTGCCTTACCTCTCCACAGCG | n-1, CT |
| 15 | EZH2_Y646H_R4 | AGTGCCTTACCTCTCCACAATG | n-2, AG |
| 16 | EZH2_Y646H_R5 | AGTGCCTTACCTCTCCACATTG | n-2, TG |
| 17 | EZH2_Y646H_R6 | AGTGCCTTACCTCTCCACACTG | n-2, CG |
| 18 | EZH2_Y646H_R7 | AGTGCCTTACCTCTCCACGGTG | n-3, GA |
| 19 | EZH2_Y646H_R8 | AGTGCCTTACCTCTCCACTGTG | n-3, TA |
| 20 | EZH2_Y646H_R9 | AGTGCCTTACCTCTCCACCGTG | n-3, CA |
| 21 | EZH2_Y646F_R | TCAGTGCCTTACCTCTCCACAGA | none |
| 22 | EZH2_Y646F_R1 | TCAGTGCCTTACCTCTCCACAAA | n-1, AG |
| 23 | EZH2_Y646F_R2 | TCAGTGCCTTACCTCTCCACATA | n-1, TG |
| 24 | EZH2_Y646F_R3 | TCAGTGCCTTACCTCTCCACACA | n-1, CG |
| 25 | EZH2_Y646F_R4 | TCAGTGCCTTACCTCTCCACGGA | n-2, GA |
| 26 | EZH2_Y646F_R5 | TCAGTGCCTTACCTCTCCACTGA | n-2, TA |
| 27 | EZH2_Y646F_R6 | TCAGTGCCTTACCTCTCCACCGA | n-2, CA |
| 28 | EZH2_Y646F_R7 | TCAGTGCCTTACCTCTCCAAAGA | n-3, AC |
| 29 | EZH2_Y646F_R8 | TCAGTGCCTTACCTCTCCAGAGA | n-3, GC |
| 30 | EZH2_Y646F_R9 | TCAGTGCCTTACCTCTCCATAGA | n-3, TC |
| 31 | EZH2_Y646S_R | TCAGTGCCTTACCTCTCCACAGG | none |
| 32 | EZH2_Y646S_R1 | TCAGTGCCTTACCTCTCCACAAG | n-1, AG |
| 33 | EZH2_Y646S_R2 | TCAGTGCCTTACCTCTCCACATG | n-1, TG |
| 34 | EZH2_Y646S_R3 | TCAGTGCCTTACCTCTCCACACG | n-1, CG |
| 35 | EZH2_Y646S_R4 | TCAGTGCCTTACCTCTCCACTGG | n-2, TA |
| 36 | EZH2_Y646S_R5 | TCAGTGCCTTACCTCTCCACCGG | n-2, CA |
| 37 | EZH2_Y646S_R6 | TCAGTGCCTTACCTCTCCACGGG | n-2, GA |
| 38 | EZH2_Y646S_R7 | TCAGTGCCTTACCTCTCCAAAGG | n-3, AC |
| 39 | EZH2_Y646S_R8 | TCAGTGCCTTACCTCTCCATAGG | n-3, TC |
| 40 | EZH2_Y646S_R9 | TCAGTGCCTTACCTCTCCAGAGG | n-3, GC |
| 41 | EZH2_Y646C_R | AGTGCCTTACCTCTCCACAGC | none |

TABLE 2-continued

Oligonucleotides for detecting mutations at position Y646

| SEQ ID NO: | Oligo_ID | Sequence | MM* location and sequence |
|---|---|---|---|
| 42 | EZH2_Y646C_R1 | AGTGCCTTACCTCTCCACAAC | n-1, AG |
| 43 | EZH2_Y646C_R2 | AGTGCCTTACCTCTCCACATC | n-1, TG |
| 44 | EZH2_Y646C_R3 | AGTGCCTTACCTCTCCACACC | n-1, CG |
| 45 | EZH2_Y646C_R4 | AGTGCCTTACCTCTCCACTGC | n-2, TA |
| 46 | EZH2_Y646C_R5 | AGTGCCTTACCTCTCCACCGC | n-2, CA |
| 47 | EZH2_Y646C_R6 | AGTGCCTTACCTCTCCACGGC | n-2, GA |
| 48 | EZH2_Y646C_R7 | AGTGCCTTACCTCTCCAGAGC | n-3, GC |
| 49 | EZH2_Y646C_R8 | AGTGCCTTACCTCTCCAAAGC | n-3, AC |
| 50 | EZH2_Y646C_R9 | AGTGCCTTACCTCTCCATAGC | n-3, TC |
| 51 | EZH2-WT_Y646_R | TCAGTGCCTTACCTCTCCACAGTA | None (WT) |

| SEQ ID NO: | Oligo_ID | Sequence | Function |
|---|---|---|---|
| | | Other oligonucleotides | |
| 52 | EZH2_EX16_cFWD | ATTGCTGGCACCATCTGACGT | Common F Primer |
| 53 | EZH2E16_R_PRB1 | FTTTATCAAQAGATCCTGTGCAG AAAAATGAATTCATCTCAP** | Probe |
| 54 | EZEX16_CPRB3 | FTTTATCCAAAGATCCTGTGCAG AAAAATGAATTCATCTCAP** | |
| 55 | EZH2_EX16CFWD2 | TTGCTGGCACCATCTGACGTG | Common F Primer |
| 56 | EZH2_EX16CFWD3 | TATTGCTGGCACCATCTGACG | Common F Primer |
| 57 | EZH2_EX16CFWD4 | CTATTGCTGGCACCATCTGAC | Common F Primer |

*"MM (mismatch) location" indicates the distance from the 3'-end to the mismatched nucleotide. "Sequence" indicates the nucleotide change resulting in the mismatch, e.g., "AT" means that T has been replaced with a A.
**F-reporter, Q-quencher, P-phosphate group

TABLE 3

Oligonucleotides for detecting mutations at position A682

Allele-specific primers

| SEQ ID NO: | Oligo_ID | Sequence | MM* location and sequence |
|---|---|---|---|
| 58 | EZH2_A682G_WTR | CGAATTTTGTTACCCTTGCGGGTTG | None, WT |
| 59 | EZH2_A682G_R | CGAATTTTGTTACCCTTGCGGGTTC | none |
| 60 | EZH2_A682G_R1 | CGAATTTTGTTACCCTTGCGGGTAC | n-1, AT |
| 61 | EZH2_A682G_R2 | CGAATTTTGTTACCCTTGCGGGTCC | n-1, CT |
| 62 | EZH2_A682G_R3 | CGAATTTTGTTACCCTTGCGGGTAC | n-1, GT |
| 63 | EZH2_A682G_R4 | CGAATTTTGTTACCCTTGCGGGATC | n-2, AT |
| 64 | EZH2_A682G_R5 | CGAATTTTGTTACCCTTGCGGGCTC | n-2, CT |
| 65 | EZH2_A682G_R6 | CGAATTTTGTTACCCTTGCGGGGTC | n-2, GT |
| 66 | EZH2_A682G_R7 | CGAATTTTGTTACCCTTGCGGATTC | n-3, AG |
| 67 | EZH2_A682G_R8 | CGAATTTTGTTACCCTTGCGGTTTC | n-3, TG |
| 68 | EZH2_A682G_R9 | CGAATTTTGTTACCCTTGCGGCTTC | n-3, CG |

TABLE 3-continued

Oligonucleotides for detecting mutations at position A682

Other oligonucleotides

| SEQ ID NO: | Oligo_ID | Sequence | Function |
|---|---|---|---|
| 69 | EZH2_A682G_cFWD | GTTTACTTATAACTGAAATTATTCACTGGGC | F primer |
| 70 | EZ_A682G_R_fJ9 | JTGCTTACTTTTQTTCTTTTTAGATTTTGTGGTGGAP* | probe |
| 71 | EZ_A682G_R_fP1 | ETGCTTACTTTTQTTCTTTTTAGATTTTGTGGTGGAP** | probe |

*J-reporter, E-reporter, Q-quencher, P-phosphate

TABLE 4

Oligonucleotides for detecting mutations at position A692

Allele-specific primers

| SEQ ID NO: | Oligo_ID | SEQUENCE | MM* location and sequence |
|---|---|---|---|
| 72 | EZH2_A692V_WT_R | TAGCAGTTTGGATTTACCGAATGATTTG | None, WT |
| 73 | EZH2_A692V_R | TAGCAGTTTGGATTTACCGAATGATTTA | None |
| 74 | EZH2_A692V_R1 | TAGCAGTTTGGATTTACCGAATGATTAA | n-1, AT |
| 75 | EZH2_A692V_R2 | TAGCAGTTTGGATTTACCGAATGATTCA | n-1, CT |
| 76 | EZH2_A692V_R3 | TAGCAGTTTGGATTTACCGAATGATTGA | n-1, GT |
| 77 | EZH2_A692V_R4 | TAGCAGTTTGGATTTACCGAATGATATA | n-2, AT |
| 78 | EZH2_A692V_R5 | TAGCAGTTTGGATTTACCGAATGATCTA | n-2, CT |
| 79 | EZH2_A692V_R6 | TAGCAGTTTGGATTTACCGAATGATGTA | n-2, GT |
| 80 | EZH2_A692V_R7 | TAGCAGTTTGGATTTACCGAATGAATTA | n-3, AT |
| 81 | EZH2_A692V_R8 | TAGCAGTTTGGATTTACCGAATGACTTA | n-3, CT |
| 82 | EZH2_A692V_R9 | TAGCAGTTTGGATTTACCGAATGAGTTA | n-3, GT |
| 83 | EZH2_A692V_R1F | TAGCAGTTTGGATTTACCGAATGATTFA* | n-1, FT |

Other oligonucleotides

| SEQ ID NO: | Oligo_ID | Sequence | Function |
|---|---|---|---|
| 84 | EZH2_A692V_cFWD | CACTGGGCTGTGCTTACTTTTTTC | F primer |
| 85 | EZH2_A692V_R_fP1 | ETTTAGATQTTTGTGGTGGATGCAACCCGCAAP** | Probe |

*F-N6 methyl-dA
**E-reporter, Q-quencher, P-phosphate

In another embodiment, the present invention is a diagnostic method of detecting EZH2 mutations using the oligonucleotides disclosed in Tables 2-4. The method comprises contacting a test sample containing nucleic acid with one or more allele-specific primers for an EZH2 mutation selected from Tables 2-4 in the presence of the corresponding second primer, (optionally, also selected from Tables 2-4), nucleoside triphosphates and a nucleic acid polymerase, such that the one or more allele-specific primers is efficiently extended only when an EZH2 mutation is present in the sample; and detecting the presence or absence of an EZH2 mutation by detecting the presence or absence of the extension product.

In a particular embodiment the presence of the extension product is detected with a probe. In variations of this embodiment the probe is selected from Tables 2-4. The probe may be labeled with a radioactive, a fluorescent or a chromophore label. For example, the mutation may be detected by detecting amplification of the extension product by real-time polymerase chain reaction (rt-PCR), where hybridization of the probe to the extension product results in enzymatic digestion of the probe and detection of the resulting fluorescence (TaqMan™ probe method, Holland et al. (1991) P.N.A.S. USA 88:7276-7280). The presence of the amplification product in rt-PCR may also be detected by detecting a change in fluorescence due to the formation of a nucleic acid duplex between the probe and the extension product. (U.S. application Ser. No. 12/330,694, filed on Dec. 9, 2008). Alternatively, the presence of the extension product and the amplification product may be detected by gel electrophoresis followed by staining or by blotting and hybridization as described e.g., in Sambrook, J. and Russell, D. W. (2001) *Molecular Cloning*, 3$^{rd}$ ed. CSHL Press, Chapters 5 and 9.

In yet another embodiment, the invention is a combination of oligonucleotides for simultaneously detecting mutations at positions Y646, A682 and A692 in the human EZH2 gene. In variations of this embodiment, the combination comprises at least one allele-specific primer from each of Tables 2-4 and optionally, at least one common primer from each of Tables 2-4, and further optionally, at least one probe from each of Tables 2-4. As demonstrated e.g., in Table 5, the isolated oligonucleotides of the present invention are uniquely suitable for being combined in testing kits. Table 5 demonstrates that each oligonucleotide is specific for its target mutation even with the closely related mutation is present in the sample.

In another embodiment, the invention is a method of treating a patient having a tumor possibly harboring cells with a mutant EZH2 gene. The method comprises contacting a sample from the patient with one or more allele-specific primers for an EZH2 mutation selected from Tables 2-4 in the presence of a corresponding second primer or primers, (optionally, also selected from Tables 2-4), conducting allele-specific amplification, and detecting the presence or absence of an EZH2 mutation by detecting presence or absence of the extension product, and if at least one mutation is found, administering to the patient a compound that inhibits signaling of the mutant EZH2 protein encoded by the mutated gene. In variations of this embodiment, the EZH2 inhibitor is selected from EI1 (Qi, W., et al. (2012) PNAS USA 109(52):21360); EPZ6438-E7438 (Knutson, S. K., et al. (2012) Nat Chem Biol. 8(11):890; GSK343 or GSK126 (McCabe, M. T., et al. (2012) Nature 108:108; or any other suitable selective EZH2 inhibitor that is or will become available.

In yet another embodiment, the invention is a kit containing reagents necessary for detecting mutations in the EZH2 gene. The reagents comprise one or more allele-specific primers for an EZH2 mutation selected from Tables from each of Tables 2-4, one or more corresponding second primers (optionally also selected from Tables from each of Tables 2-4), and optionally, one or more probes (optionally also selected from Tables from each of Tables 2-4). The kit may further comprise reagents necessary for the performance of amplification and detection assay, such as nucleoside triphosphates, nucleic acid polymerase and buffers necessary for the function of the polymerase. In some embodiments, the probe is detectably labeled. In such embodiments, the kit may comprise reagents for labeling and detecting the label.

EXAMPLES

Exemplary Reaction Conditions

The exemplary reaction conditions used for testing the performance of the primers are as follows. A PCR mixture including 50 mM Tris-HCl (pH 8.0), 75-90 mM potassium chloride, 160 µM each dATP, dCTP and dGTP, 320 µM dUTP, 0.075-0.2 µM each of selective and common primer, 0.05-0.1 µM probe, target DNA (100 and 10,000 copies of a recombinant plasmid with a mutant, or 10,000 copies of wild-type genomic DNA (pooled genomic DNA, Promega, Madison, Wis., Cat. No. DD2011), 0.2 U/uL uracil-N-glycosylase, 200 nM NTQ21-46A aptamer, 40 nM DNA polymerase, 0.1 mM EDTA, 1.25%-2% DMSO, 2.5 mM magnesium acetate. Amplification and analysis was done using the Roche LightCycler® 480 instrument (Roche Applied Science, Indianapolis, Ind.) The following temperature profile was used: 50° C. 5 minutes; 2 cycles of 95° C. (10 seconds) to 62° C. (30 seconds) followed by cycling from 93° C. (10 seconds) to 62° C. (30 seconds) 55 times, 1 cycle cool down to 37 (10 seconds), and 1 cycle cool down to 25 (10 seconds). Fluorescence data was collected at the start of each 62° C. step in the 55 cycles. Optionally, the reactions contained an endogenous positive control template.

Success of allele-specific PCR was measured by comparing the $C_t$ obtained with the target sequence and $C_t$ obtained with a non-target sequence, e.g., a different mutation or wild-type sequence at the same position.

Example 1

Primers for Detecting Mutations at Position Y646 in the Human EZH2 Gene

Primers and probes shown in Table 2 were tested under the experimental conditions set forth above. Table 5 shows amplification (as measured by $C_t$).

TABLE 5

Performance of primers at position Y646 in the human EZH2 gene

| SEQ ID NO: | Y646H* | Y646F | Y646S | Y646C | Mut/WT Mix** | Primer ID |
|---|---|---|---|---|---|---|
| 1 | 34.26 | 42.17 | 47.54 | 38.58 | 30.90 | EZH2_Y646N_R |
| 2 | 47.82 | 36.50 | 29.78 | 35.79 | 34.41 | EZH2_Y646N_R1 |
| 3 | 35.51 | 47.75 | 42.02 | 41.62 | 30.90 | EZH2_Y646N_R2 |
| 4 | 48.14 | 42.68 | 42.47 | 38.26 | 33.01 | EZH2_Y646N_R3 |
| 5 | 35.56 | 30.70 | 38.04 | 34.09 | 31.99 | EZH2_Y646N_R4 |
| 6 | 43.42 | 42.79 | 55.00 | 39.46 | 33.02 | EZH2_Y646N_R5 |
| 7 | 44.14 | 44.84 | 46.99 | 42.00 | 38.49 | EZH2_Y646N_R6 |
| 8 | 29.52 | 35.71 | 37.57 | 37.78 | 30.77 | EZH2_Y646N_R7 |
| 9 | 28.83 | 37.46 | 47.21 | 38.36 | 30.78 | EZH2_Y646N_R8 |
| 10 | 31.09 | 37.60 | 55.00 | 36.71 | 30.74 | EZH2_Y646N_R9 |
| 11 | 25.87 | 48.78 | 51.29 | 43.49 | 28.59 | EZH2_Y646H_R |
| 12 | 39.07 | 39.45 | 48.71 | 55.00 | 47.27 | EZH2_Y646H_R1 |
| 13 | 36.19 | 48.35 | 30.26 | 48.55 | 41.78 | EZH2_Y646H_R2 |
| 14 | 26.93 | 46.10 | 37.19 | 31.39 | 31.31 | EZH2_Y646H_R3 |
| 15 | 26.82 | 38.71 | 41.92 | 44.76 | 31.36 | EZH2_Y646H_R4 |
| 16 | 27.43 | 55.00 | 55.00 | 55.00 | 32.40 | EZH2_Y646H_R5 |
| 17 | 30.82 | 52.65 | 41.11 | 45.74 | 36.52 | EZH2_Y646H_R6 |
| 18 | 25.84 | 55.00 | 49.40 | 55.00 | 30.31 | EZH2_Y646H_R7 |
| 19 | 26.03 | 55.00 | 50.18 | 55.00 | 30.46 | EZH2_Y646H_R8 |
| 20 | 25.95 | 55.00 | 45.69 | 55.00 | 30.32 | EZH2_Y646H_R9 |
| 21 | 37.98 | 25.50 | 32.10 | 40.84 | 31.01 | EZH2_Y646F_R |
| 22 | 50.54 | 28.47 | 49.25 | 55.00 | 34.89 | EZH2_Y646F_R1 |

TABLE 5-continued

Performance of primers at position Y646 in the human EZH2 gene

| SEQ ID NO: | Y646H* | Y646F | Y646S | Y646C | Mut/WT Mix** | Primer ID |
|---|---|---|---|---|---|---|
| 23 | 45.35 | 28.41 | 43.39 | 44.07 | 34.44 | EZH2_Y646F_R2 |
| 24 | 30.88 | 28.96 | 27.85 | 29.12 | 30.52 | EZH2_Y646F_R3 |
| 25 | 51.19 | 25.61 | 28.78 | 39.00 | 31.22 | EZH2_Y646F_R4 |
| 26 | 50.05 | 26.26 | 37.85 | 41.62 | 31.74 | EZH2_Y646F_R5 |
| 27 | 55.00 | 25.22 | 38.65 | 39.78 | 30.89 | EZH2_Y646F_R6 |
| 28 | 41.84 | 25.37 | 48.65 | 39.30 | 31.65 | EZH2_Y646F_R7 |
| 29 | 39.69 | 25.51 | 40.73 | 40.24 | 31.24 | EZH2_Y646F_R8 |
| 30 | 40.01 | 25.36 | 45.36 | 44.63 | 30.72 | EZH2_Y646F_R9 |
| 31 | 37.50 | 29.90 | 25.27 | 33.56 | 30.76 | EZH2_Y646S_R |
| 32 | 36.94 | 35.25 | 26.79 | 33.44 | 32.58 | EZH2_Y646S_R1 |
| 33 | 35.71 | 44.05 | 26.32 | 43.26 | 31.73 | EZH2_Y646S_R2 |
| 34 | 55.00 | 55.00 | 30.09 | 55.00 | 43.81 | EZH2_Y646S_R3 |
| 35 | 44.38 | 40.31 | 25.09 | 42.49 | 30.87 | EZH2_Y646S_R4 |
| 36 | 38.92 | 35.91 | 24.94 | 34.12 | 30.63 | EZH2_Y646S_R5 |
| 37 | 38.53 | 39.11 | 24.94 | 41.34 | 30.59 | EZH2_Y646S_R6 |
| 38 | 42.98 | 44.23 | 25.50 | 35.28 | 31.23 | EZH2_Y646S_R7 |
| 39 | 37.98 | 39.91 | 25.03 | 40.85 | 30.93 | EZH2_Y646S_R8 |
| 40 | 55.00 | 55.00 | 41.56 | 55.00 | 51.47 | EZH2_Y646S_R9 |
| 41 | 27.90 | 31.06 | 43.15 | 25.25 | 28.67 | EZH2_Y646C_R |
| 42 | 42.03 | 55.00 | 55.00 | 26.14 | 31.09 | EZH2_Y646C_R1 |
| 43 | 45.47 | 55.00 | 55.00 | 26.79 | 31.68 | EZH2_Y646C_R2 |
| 44 | 44.28 | 48.93 | 46.45 | 30.05 | 36.71 | EZH2_Y646C_R3 |
| 45 | 38.69 | 55.00 | 55.00 | 25.52 | 30.27 | EZH2_Y646C_R4 |
| 46 | 37.63 | 45.69 | 55.00 | 25.48 | 30.20 | EZH2_Y646C_R5 |
| 47 | 38.32 | 50.07 | 55.00 | 25.40 | 30.07 | EZH2_Y646C_R6 |
| 48 | 39.69 | 55.00 | 55.00 | 25.38 | 30.13 | EZH2_Y646C_R7 |
| 49 | 40.88 | 55.00 | 55.00 | 25.56 | 30.12 | EZH2_Y646C_R8 |
| 50 | 38.56 | 55.00 | 55.00 | 25.61 | 30.10 | EZH2_Y646C_R9 |

*In these reactions, the template was a pure sample of mutant DNA
**In these reactions, the template was a mixture of the targeted mutation and wild-type DNA Example 2

Primers for Detecting Mutations at Position A682 in the Human EZH2 Gene

Primers and probes shown in Table 3 were tested under the experimental conditions set forth above. Table 6 shows amplification specificity as measured by $C_t$ and $\Delta C_t$ (between the matched (mutant) and mismatched (wild-type) templates.).

TABLE 6

Performance of primers at position A682 in the human EZH2 gene

| | Primer | | | | | | | | | | |
|---|---|---|---|---|---|---|---|---|---|---|---|
| | R | R1 | R2 | R3 | R4 | R5 | R6 | R7 | R8 | R9 | WT |
| SEQ ID NO: | 59 | 60 | 61 | 62 | 63 | 64 | 65 | 66 | 67 | 68 | 58 |
| Mut/wt Target | 30.51 | 35.56 | 30.61 | 33.81 | 29.17 | 28.86 | 31.62 | 28.54 | 28.36 | 29.01 | 39 |
| WT Target | 39.9 | 44.76 | 44.28 | 24.35 | 39.12 | 40.86 | 32.92 | 43.04 | 32.85 | 38.88 | 21.75 |
| ΔCt | 9.39 | 9.2 | 13.67 | −9.46 | 9.95 | 12 | 1.31 | 14.51 | 4.49 | 9.87 | — |

Example 3

Primers for Detecting Mutations at Position A692 in the Human EZH2 Gene

Primers and probes shown in Table 4 were tested under the experimental conditions set forth above. Table 7 shows amplification specificity as measured by $C_t$ and $\Delta C_t$ (between the matched (mutant) and mismatched (wild-type) templates.).

TABLE 7

Performance of primers at position A682 in the human EZH2 gene

| | Template | | | | | | | | | | |
|---|---|---|---|---|---|---|---|---|---|---|---|
| | R | R1 | R2 | R3 | R4 | R5 | R6 | R7 | R8 | R9 | WTR |
| SEQ ID NO: | 59 | 60 | 61 | 62 | 63 | 64 | 65 | 66 | 67 | 68 | 58 |
| Wt/mut target | 25.84 | 28.58 | 26.59 | 55 | 55 | 55 | 27.6 | 26.2 | 26.11 | 26.29 | 26.67 |
| WT target | 22.3 | 38.18 | 33.13 | 55 | 55 | 55 | 33.67 | 32.67 | 32.18 | 32.15 | 18.72 |
| ΔCt | −3.54 | 9.6 | 6.54 | N/A | N/A | N/A | 6.07 | 6.48 | 6.07 | 5.86 | −7.95 |

While the invention has been described in detail with reference to specific examples, it will be apparent to one skilled in the art that various modifications can be made within the scope of this invention. Thus the scope of the invention should not be limited by the examples described herein, but by the claims presented below.

What is claimed is:

1. An isolated oligonucleotide comprising the sequence of SEQ ID NO:11, the oligonucleotide differing from SEQ ID NO:11 by-at least one substitution modification in SEQ ID NO:11, wherein the oligonucleotide does not include the sequence of SEQ ID NOs:1, 21, 31, 41, or 51, wherein the substitution modification is located within the last 4 nucleotides at the 3'-end of the oligonucleotide, but not at the position corresponding to nucleotide 22 of SEQ ID NO:11, and wherein the oligonucleotide comprises at least one modified nucleotide, wherein the modified nucleotide has a modification selected from a modification to a nitrogenous base, sugar, or backbone of the modified nucleotide.

2. The isolated oligonucleotide of claim 1 selected from the group consisting of SEQ ID NOs:16 and 18-20.

3. A method of detecting a mutation in human EZH2 nucleic acid in a nucleic acid sample comprising:
   (a) contacting the nucleic acid sample with the oligonucleotide of claim 1;
   (b) incubating the nucleic acid sample under conditions allowing hybridization of the oligonucleotide to the target sequence within the EZH2 nucleic acid;
   (c) generating an amplification product containing the target sequence within the EZH2 nucleic acid; and
   (d) detecting the presence of the amplified product thereby detecting the presence of the mutation in the EZH2 nucleic acid.

4. The method of claim 3, wherein the nucleic acid sample is obtained from blood, plasma, serum, or a formaldehyde fixed paraffin-embedded tissue sample.

5. A kit comprising the oligonucleotide of claim 1 and at least one additional reagent for use in PCR.

6. The kit of claim 5, wherein the oligonucleotide is selected from SEQ ID NOs:16 and 18-20.

7. The kit of claim 5, further comprising a probe specific for a region of the human EZH2 gene sequence within 100 nucleotides from the sequence encoding Y646, wherein the probe is labeled with a reporter and a quencher.

8. The kit of claim 5, further comprising a second oligonucleotide comprising the sequence of SEQ ID NO:21, the second oligonucleotide differing from SEQ ID NO:21 by at least one substitution mutation in SEQ ID NO:21, wherein the second oligonucleotide does not include the sequence of SEQ ID NOs:1, 11, 31, 41, or 51, and wherein the substitution modification is located within the last 4 nucleotides at the 3'-end of the second oligonucleotide, but not at the position corresponding to nucleotide 23 of SEQ ID NO:21.

9. The kit of claim 5, further comprising a second oligonucleotide comprising the sequence of SEQ ID NO:41, the second oligonucleotide differing from SEQ ID NO:41 by at least one substitution modification in SEQ ID NO:41, wherein the second oligonucleotide does not include the sequence of SEQ ID NOs:1, 11, 31, or 51, and wherein the substitution modification is located within the last 4 nucleotides at the 3'-end of the second oligonucleotide, but not at the position corresponding to nucleotide 21 of SEQ ID NO:41.

10. The kit of claim 5, further comprising a second oligonucleotide comprising the sequence of SEQ ID NO:59, except comprising at least one substitution modification, wherein the second oligonucleotide does not include the sequence of SEQ ID NO:58, and wherein the substitution modification is located within the last 4 nucleotides at the 3'-end of the second oligonucleotide, but not at the position corresponding to nucleotide 25-of SEQ ID NO:59.

11. The kit of claim 5, further comprising a second oligonucleotide comprising the sequence of SEQ ID NO:73, except comprising at least one substitution modification, wherein the oligonucleotide does not include the sequence of SEQ ID NO:71, and wherein the substitution modification is located within the last 4 nucleotides at the 3'-end of the second oligonucleotide, but not at the position corresponding to nudeotide 28 of SEQ ID NO:73.

12. The oligonucleotide of claim 1, wherein the oligonucleotide consists of the sequence of SEQ ID NO:11 with one substitution modification.

* * * * *